US006757618B2

(12) United States Patent
Johnson et al.

(10) Patent No.: US 6,757,618 B2
(45) Date of Patent: Jun. 29, 2004

(54) CHEMICAL STRUCTURE IDENTIFICATION

(75) Inventors: Mark A. Johnson, Kalamazoo, MI (US); Yong-jin Xu, St. Louis, MO (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 331 days.

(21) Appl. No.: 09/851,845

(22) Filed: May 9, 2001

(65) Prior Publication Data

US 2002/0022933 A1 Feb. 21, 2002

Related U.S. Application Data

(60) Provisional application No. 60/202,624, filed on May 9, 2000.

(51) Int. Cl.[7] .............................................. G01N 33/00
(52) U.S. Cl. ........................................ 702/27; 435/287
(58) Field of Search .............................. 702/19, 22–23, 702/27, 30–32; 435/287.1, 288.7; 700/266, 213–215, 225–226

(56) References Cited

U.S. PATENT DOCUMENTS

| | | | | | |
|---|---|---|---|---|---|
| 4,719,582 | A | * | 1/1988 | Ishida et al. ................... | 702/27 |
| 4,751,077 | A | * | 6/1988 | Bell et al. ................... | 424/85.6 |
| 4,855,931 | A | | 8/1989 | Saunders ..................... | 364/499 |
| 5,752,019 | A | | 5/1998 | Rigoutsos et al. .......... | 395/603 |
| 5,784,294 | A | | 7/1998 | Platt et al. ................... | 364/496 |
| 5,880,972 | A | * | 3/1999 | Horlbeck ..................... | 702/27 |
| 6,038,514 | A | * | 3/2000 | Nozaki ........................ | 702/27 |
| 6,182,016 | B1 | * | 1/2001 | Liang et al. ................... | 702/22 |
| 6,199,017 | B1 | * | 3/2001 | Tomonaga et al. ............ | 702/19 |
| 6,219,622 | B1 | * | 4/2001 | Schmidt ....................... | 702/27 |
| 6,295,514 | B1 | * | 9/2001 | Agrafiotis et al. ............ | 703/12 |

FOREIGN PATENT DOCUMENTS

WO    WO 00/20991    4/2000

OTHER PUBLICATIONS

Behzad, M., Chartrand, G., Lesniak–Foster, L.; *Graphs and Digraphs*; Prindle, Weber & Schmidt; 1979; p. 4.

Bemis, GW., Murcko, MA.; *The Properties of Known Drugs*. 1. Molecular Frameworks; J Med Chem 1996; 39: pp. 2887–2893.

Feller, W. In: *An Introduction to Probability Theory and It's Applications*; John Wiley & Sons, 1971; Chapter 2 Section 5; pp. 53–55.

Morgan, HL.; *The Generation of a Unique Machine Description for Chemical Graphs—A Technique Developed at Chemical Abstracts Service*. J. Chem. Doe. 1965;5: pp. 107–113.

Nilakantan, R., Bauman, N., Haraki, K., Venkatarahavan, RA.; *Ring–Based Chemical Structural Query System: Use of a Novel Ring–Complexity Heuristic*; J. Chem. Inf. Comput. Sci. 1990;30: pp. 65–68.

Randić, M.; *On Unique Numbering of Vertices and Unique Codes for Molecular Graphs*; J. Chem. Inf. Comput. Sci. 1975;15: pp. 105–108.

(List continued on next page.)

*Primary Examiner*—Marc S. Hoff
*Assistant Examiner*—Mary Catherine Baran
(74) *Attorney, Agent, or Firm*—Pharmacia & Upjohn Company; Thomas A. Wootton

(57) ABSTRACT

A method for generating a numeric or alpha-numeric identifier representative of a chemical structure having at least two atoms connected by a bond includes the step of assigning a numerical value to each atom and a numerical bond value to each bond. The method updates the numerical values for each atom based on the current values assigned to each atom and the numerical bond value. After the numerical values for each atom have been updated the method calculates a numeric or alpha-numeric identifier for the chemical structure.

25 Claims, 9 Drawing Sheets

OTHER PUBLICATIONS

Randić, M., Wipke, WT., Cramer, RD. III, Howe, WJ; *Techniques for Perception by a Computer of Synthetically Significant Structural Features in Complex Molecules*; J. Am. Chem. Soc. 1972;94: pp. 431–439.

Read, RC., Corneil, DG.; *The Graph Isomorphism Disease*; J. Graph Theory 1977;1: pp. 339–363.

Shelley CA, Muck ME.; *An Approach to the Assignment of Canonical Connection Tables and Topological Symmetry Perception*; J. Chem. Inf. Comput. Sci. 1979;19: pp. 247–250.

Spotfire is a commerical data visualization package marketed by Spotfire AB, Göteberg, Sweden; http://www.spotfire.com; pp. 1–2; Sep. 10, 2001.

Uchnio, M.; *Algorithm for Unique and Unambiguous Coding and Symmetry Perception of Molecular Graph Diagram. I. Vector Functions for Automorphism Partitioning*; J. Chem. Inf. Comput. Sci. 1980;20: pp. 116–120.

Zheng, O., Yuan, S., Brandt, J., Zheng, C.; *An Effective Topological Symmetry Perception and Unique Numbering Algorithm*; J. Chem. Inf. Comput. Sci. 1999;39: pp. 299–303.

International Search Report (counterpart PCT application).

Johnson, Browsable Structure–Activity Datasets, Advances in Molecular Similarity, 2: 153–170 (1998).

* cited by examiner

CHEMICAL STRUCTURE IDENTIFICATION

CROSS REFERENCE TO RELATED APPLICATION

This application claims the benefit of U.S. Provisional application No. 60/202,624 filed on May 9, 2000.

TECHNICAL FIELD

The present invention relates to chemical structures and, more particularly, to a method and apparatus for assigning numeric or alpha-numeric identifiers to chemical structures and for identifying chemical equivalency.

BACKGROUND ART

In the field of chemistry there are numerous molecular properties that are of possible interest to chemists. Molecules may be compared for equivalency based on these properties. For example, a high level or general comparison of equivalency may compare two compounds or molecules with respect to the number of non-hydrogen atoms they contain or the number of bonds they have. Alternatively, a more detailed comparison of equivalency may compare chemical structures based not only on the number of bonds or atoms, but on specific atomic connectivity or spatial relationships of those atoms. For example, ring systems or cyclic systems of two molecules or compounds may be compared for equivalency.

A cyclic system is a chemical structure in which atoms are bonded together to form single or multiple rings. Cyclic system equivalence is of particular interest in the field of medicinal chemistry where the equivalency of cyclic systems may correspond to physiological or biological properties. However, a particular criterion of molecular equivalence only becomes operable, in a practical sense, when a chemist can identify each of the distinct classes of molecules that are equivalent with respect to the properties of interest.

Relative and absolute identification schemes are commonly used for identifying chemical structures that are molecularly equivalent. Relative identification schemes assign a unique identifier to each molecular structure encountered by the identification scheme. The assigned identifiers are not related to any particular information in a chemical structure. For example, a relative identification scheme may assign an identifier of one to a first chemical structure, an identifier of two to a second chemical structure and so on. A relative identification scheme, therefore, requires a memory that stores a list of identifiers that have been previously assigned to molecular structures.

An absolute identification scheme assigns an identifier to a molecular structure based solely on the information available in the molecular structure being identified. For example, an absolute identification scheme may assign a chemical structure having three atoms and two bonds, the identifier 32, wherein the first digit represents the number of atoms in the structure and the second digit represents the number of bonds in the structure. Absolute identification schemes are beneficial in that the scheme need not check to see if an identifier is in use when assigning a new identifier. Additionally, through the use of an absolute identification system, two collections of compounds (e.g., molecular structures) may be directly compared with respect to the molecules they contain without coordinating their identifiers.

Criteria of equivalence are useful when a chemist is selecting compounds (e.g., collections or mixtures of molecules) for purchase. When selecting compounds for purchase, the chemist may first filter the list of compounds to screen out the compounds that are clearly of no interest. After screening out the uninteresting compounds, the chemist may visually inspect the remaining compounds. The chemist may sort the remaining compounds according to their cyclic system identifiers and, therefore, may include or exclude portions of compounds having common cyclic system identifiers. In selecting compounds for purchase, the use of cyclic system identification may save time and reduce error in selecting compounds for purchase. However, if a particular identification system erroneously assigns the same cyclic system identifier to compounds having different cyclic systems, the chemist loses faith in the fidelity of the identification system and the ability of the identification system to distinguish different chemical structures.

Criteria of equivalence are also useful in comparing two or more different collections of compounds. For example, if a chemist desires to know which compounds are similar with regard to particular properties among compound collections and which compounds differ with regard to particular properties among the compound collections, the chemist may use an identification system to name or identify each compound in the two compound collections. If the identification system the chemist uses is an absolute identification system, the chemist may simply compare the identifiers of the chemical structures of the compounds in the two compound collections. An identifier common to the compound collections indicates a common compound between the compound collections. A unique identifier in one of the collections indicates a compound found only in that collection.

In chemical and drug research, chemists often construct compound screening collections or libraries. Screening collections are used to scan a subset of a collection of compounds for a particular activity, rather than scanning the entire compound collection. The subset could be designed to emphasize particular types of compounds or could be designed to contain dissimilar compounds. If the cyclic systems of the compounds are used as a typing criterion for the collection, screening subsets are easily constructed. For example, after the chemist uses a filtering process to exclude compounds that the chemist does not wish to consider, the chemist may randomly order the cyclic-system identifiers and then select the number of compounds the chemist wishes from each successive cyclic system group until the chemist has a subset of the desired size.

If a screening operation has a large number of active compounds (compounds active in a biological test system of interest to a project team), the task of focusing on which of those compounds (called leads or hits) to pursue as useful starting points for lead optimization can be difficult. Numerous factors enter into the evaluation of a lead and, in many cases, close analogs of an active compound exist which differ at only one position by a small structural change from the active compound. A structure activity relationship (SAR) is sometimes said to exist if a chemist finds pairs of close analogs that differ significantly in their activity. Grouping compounds by cyclic system greatly accelerates and systematizes the process of finding such pairs. Finding such an SAR supports the choice of that cyclic system for one criterion to be used in finding leads.

In lead optimization efforts, large numbers of closely related compounds may be synthesized and tested. These efforts are guided by a growing understanding of the related SARs. SARs evolve out of numerous pairwise comparisons of closely related structures. If N compounds related to a lead exist there are $N(N-1)/2$, or roughly $N^2/2$, possible pairwise comparisons that must be considered. If N is between 1,000 and 10,000, there may be between roughly 500,000 and 50,000,000 pairwise comparisons.

Obviously, in practice most pairwise comparisons are never made. Instead the comparisons that are considered are restricted to much smaller subgroups of compounds. For a subgroup 1/Kth the size of N, there are roughly $(N/K)^2/2$, pairwise comparisons per group. Thus, if N is between 1000 and 10,000, and the subgroup size K is 1/100 the size of N, there may be between roughly 50 and 5,000 pairwise comparisons. With such efficiency gains in subgrouping, there is a compelling interest in a flexible and fast way of forming and organizing subgroups. Such a flexible and fast technique is provided by using identified cyclic systems.

A cyclic system browsing index partitions a large compound collection into interesting and non-overlapping subgroups, and thereby, enables a user to realize the preceding efficiencies in constructing useful pairwise comparisons. Constructing a comparable number of subgroups using conventional substructure and similarity searching methods is a time consuming and error prone operation.

As will be appreciated by those having ordinary skill in the art, highly accurate schemes for identification chemical structures based chemical graphs or pseudographs play a key role in the foregoing applications. An accurate identification system facilitates high-throughput browsing, grouping and searching of chemical databases. One absolute identification scheme commonly referred to as the "Morgan Algorithm" was proposed in "The Generation of a Unique Machine Description for Chemical Graphs—A Technique Developed at Chemical Abstracts Service," *J Chem DoE* 5:107, 1965. As shown in FIG. 1, a process representative of the Morgan Algorithm 10 includes various steps that may be executed on a processor, a computer, or the like. At step 12, the Morgan Algorithm 10 receives a chemical diagram, which may be in the form of a computer file. Step 14 processes the chemical diagram by assigning to each vertex (i) of the chemical structure an initial vertex value.

After each vertex (i) of the chemical structure has been assigned an initial value, step 16 updates the value of each vertex (i). In particular, for each vertex (i) step 16 sums the vertex values for the vertices connected to the vertex in question and assigns the sum to vertex in question. A mathematical representation of the operation performed by step 16 is shown below in Equation 1.

$$v_i' = \sum_j v_j \quad \text{Equation 1}$$

Wherein $v_i'$ is the updated vertex value for vertex i, j is an index representative of the vertices connected to vertex i and $v_j$ is the value of vertex j. Equation 1 is repeated for each value of i (i.e., for each vertex), wherein the number of values of i is equal to the number of vertices in the chemical graph.

Step 18 determines whether the Morgan Algorithm 10 has iterated sufficiently to converge to a numerical identifier for the chemical structure. If the Morgan Algorithm 10 has not sufficiently iterated to converge, control passes from step 18 to step 16, wherein the value of each vertex is again updated. If, however, the Morgan Algorithm 10 has sufficiently iterated, control passes from step 18 to step 20, wherein the Morgan Algorithm 10 assigns a numerical identifier (ID) or numerical name to the chemical structure. Step 20 may be carried out by taking the sum or the product of all of the vertex values for the chemical structure.

When operating on certain chemical structures, the Morgan Algorithm may not converge to a unique solution and may fail to distinguish non-isomorphic chemical structures. Therefore, the Morgan Algorithm is less accurate than is desired by chemists and the like. An algorithm capable of distinguishing all non-isomorphic chemical graphs does not presently exist.

SUMMARY OF THE INVENTION

According to one aspect, the present invention may be embodied in a method of generating a numerical identifier representative of a chemical structure having a first atom of a first type, a second atom of a second type and a bond connecting the first atom and the second atom. The method may include the steps of representing the first atom with a first numerical value, representing the second atom with a second numerical value and representing the bond with a numerical bond value. The method may further include the steps of determining a number of bridge bonds that are found in the chemical structure, calculating an updated first numerical value based on the first numerical value, the second numerical value and the numerical bond value, calculating an updated second numerical value based on the second numerical value, the first numerical value and the numerical bond value and calculating the numerical identifier based on the updated first numerical value, the updated second numerical value and the number of bridge bonds.

In some embodiments, the steps of representing the first and second atoms with first and second numerical values may include the step of representing the first and second atoms with different numerical values if the first and second atom types are not similar or representing the first and second atoms with identical numerical values if the first and second atom types are similar.

In certain embodiments, the first and second atoms may be represented by first and second chemical symbols having first and second sets of characters, wherein the steps of representing the first and second atoms with first and second numerical values may include the steps of setting the first numerical value equivalent to an ASCII code sum of the first set of characters and setting the second numerical value equivalent to an ASCII code sum of the second set of characters.

Additionally, the bond connecting the first atom and the second atom may have a bond type and the step of representing the bond with a numerical bond value may comprise representing the bond with a numerical bond value that is related to the bond type. The numerical bond identifier may be divided by a factor of two if more than one bond connects the first atom and the second atom. If the bond type is a single, double, triple or aromatic bond, the step of representing the bond with a numerical bond value may include the step of making the numerical bond value equal to one, two, three or four, respectively.

The method may further include the step of scaling the updated first and second numerical values using a modulus operation. Additionally, the method may include the step of generating an array of prime numbers, the array having a size at least as large as the update first numerical value and the updated second numerical value, wherein the step of calculating the numerical identifier is based on the array of prime numbers.

According to a second aspect, the present invention may be used on a processor and embodied in a system for generating a numerical identifier representative of a chemical structure having a first atom of a first type, a second atom of a second type and a bond connecting the first atom and the second atom. The system may include a computer readable medium communicatively coupled to the processor, a first portion of software stored on the computer readable medium and adapted to be executed on the processor to represent the first atom with a first numerical value and to represent the second atom with a second numerical value, a second portion of software stored on the memory and adapted to be executed on the processor to represent the bond with a numerical bond value, a third portion of software stored on the computer readable medium and adapted to be executed on the processor to determine a number of bridge bonds found in the chemical structure and a fourth portion of software stored on the computer readable medium and adapted to be executed on the processor to calculate an updated first numerical value based on the first numerical value, the second numerical value and the numerical bond value. The system may further include a fifth portion of software stored on the computer readable memory and adapted to be executed on the processor to calculate an updated second numerical value based on the second numerical value, the first numerical value and the numerical bond value and a sixth portion of software stored on the computer readable medium and adapted to be executed on the processor to calculate the numerical identifier based on the updated first numerical value, the updated second numerical value and the number of bridge bonds.

According to a third aspect, the present invention may be embodied in a method of compiling a library for drug research, wherein the library may include a number of identifiers representative of a number of chemical structures. The method may include the steps of selecting a chemical structure from the number of chemical structures, the selected chemical structure having a first atom, a second atom and a bond connecting the first atom and the second atom, representing the first atom with a first numerical value, representing the second atom with a second numerical value, representing the bond with a numerical bond value, calculating an updated first numerical value based on the first numerical value, the second numerical value and the numerical bond value, and calculating an updated second numerical value based on the second numerical value, the first numerical value and the numerical bond value. The method may also include the step of calculating the identifier based on the updated first numerical value and the updated second numerical value and storing the identifier in a memory. Additionally, the method may include the step of determining a number of bridge bonds in the chemical structure and using that number of bridge bonds to calculate the identifier.

In some embodiments the method may be repeated for each chemical structure in the number of chemical structures, thereby storing the number of identifiers in the memory.

In certain embodiments, the method may also include the steps of searching the memory for chemical structures having a desired attribute and outputting a list of chemical structures having the desired attribute. The list of chemical structures may then be used to select a compound for medical treatment.

Additionally, or alternatively, the method may also include the steps of sorting the number of identifiers in the memory according to a desired attribute and outputting a sorted list of chemical structures sorted according to the desired attribute. The sorted list of chemical structures to select a compound for medical treatment.

In other embodiments, the library may be a first library, the number of identifiers may be a first number of identifiers and the number of chemical structures may be a first number of chemical structures, and the method further include the step of compiling a second library including a second number of identifiers representative of a second number of chemical structures. The method may then compare the first number of identifiers with the second number of identifiers.

These and other features of the present invention will be apparent to those of ordinary skill in the art in view of the description of the preferred embodiment, which is made to the drawings, which are briefly described below.

DESCRIPTION OF THE PREFERRED EMBODIMENTS

Various embodiments of a system and method for identifying molecular structures, chemical structures or labeled pseudographs are described herein. The disclosed embodiments consider not only the atoms contained in a chemical structure, but also consider the bond types between atoms in the chemical structure. The embodiments are described below and operative descriptions of the various embodiments are provided with respect to chemical structures and pseudographs.

Figure 1:
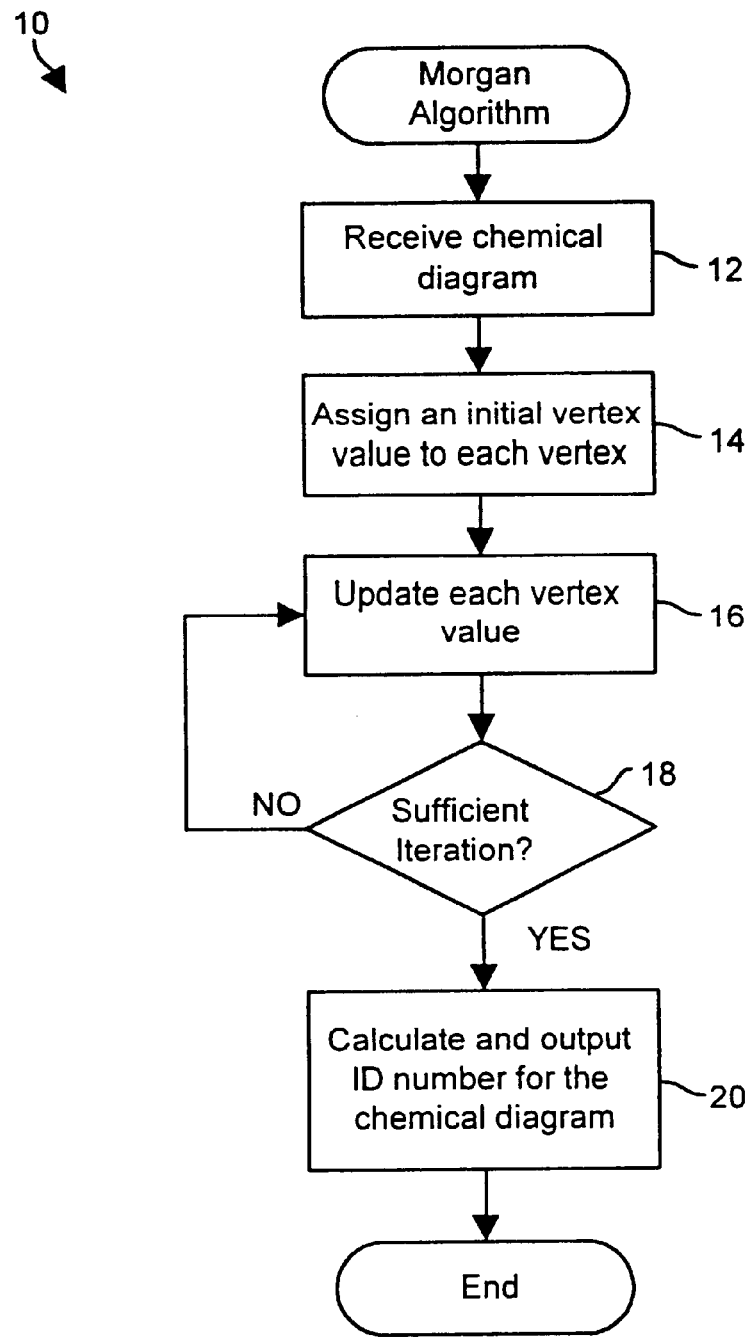
FIG. 1 is a flow diagram illustrating a prior art Morgan Algorithm process that may be used for naming chemical structures.
Figure 2:
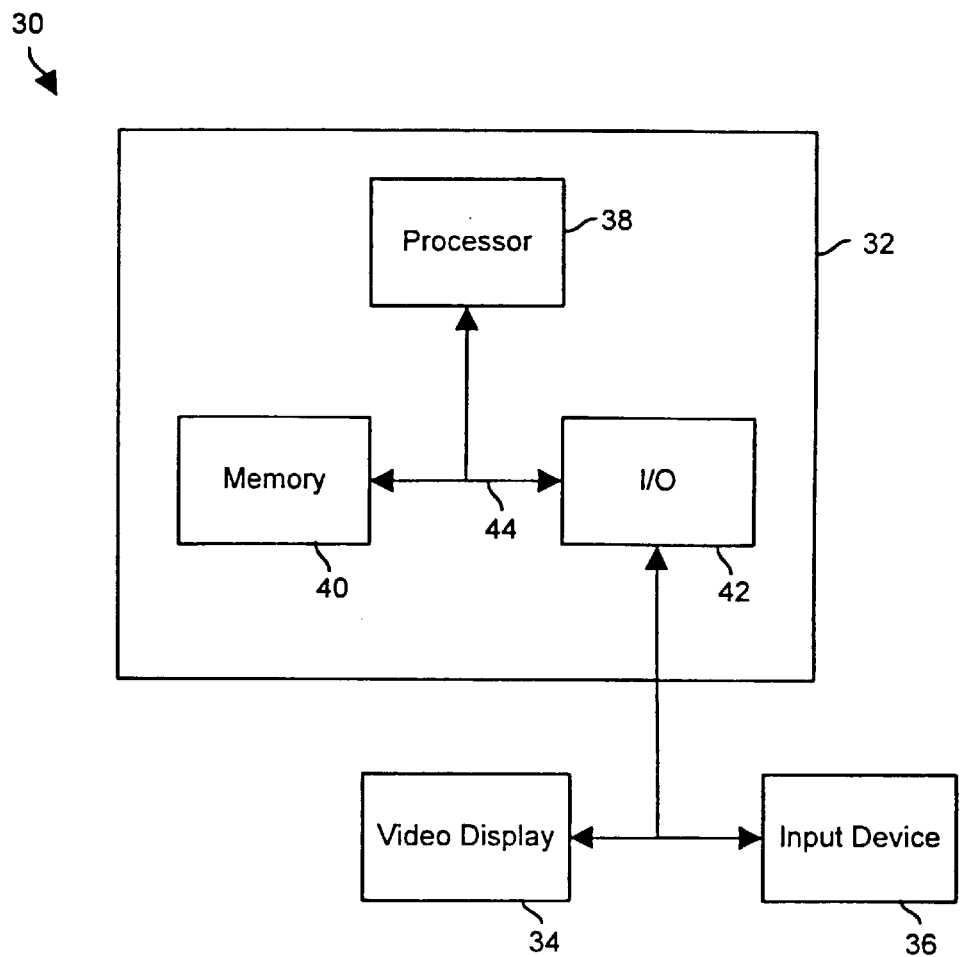
FIG. 2 is a block diagram of a computing terminal on which the methods of the present invention may be carried out.

Turning now to the figures, as shown in FIG. 2, a computing terminal 30 on which the embodiments disclosed herein may operate may include a processing unit 32, a video display 34 and an input device 36. The video display 34 may be a cathode ray tube (CRT), a liquid crystal display (LCD) or any other commercially available visual display device adapted to receive information from the processing unit 32 and display information to a user at the computing terminal. The input device 36 may be a keyboard, a mouse, a pointing device, a touch screen or any other device that may be interfaced to the processing unit 32 to enable a user at the computing terminal 30 to provide input information to the processing unit 32. Additionally, the input device 36 may be a disk drive or a network connection adapted to couple data from a data file into the processing unit 32.

In general, the processing unit 32 may be a commercially available personal computer (PC) compatible processing unit capable of operating on a Windows NT® platform. Alternatively, the processing unit 32 may be a UNIX-based workstation available from various companies such as, for example, SGI or any other type of workstation running any operating system. The processing unit 32 may include a processor 38, which may be coupled to a memory 40 and an input/output (I/O) circuit 42, via a communication bus 44. The processor 38 may be a Pentium class processor or the like. Alternatively, the processor 38 may be more powerful than a Pentium class processor. Additionally, although only one processor 38 is shown in FIG. 2, the processing unit 32 may include multiple processors.

The memory 40 may be read only memory (ROM), random access memory (RAM) or some combination thereof. In practice the memory 40 may also be a computer readable medium such as a hard drive or some other mass storage media, such as an optical disk adapted to be read by an optical drive. Additionally, while the memory 40 is shown inside the processing unit 32 of FIG. 2, the memory 40 could be external to the processing unit 32. For example, the memory 40 could be located at a server (not shown) that is at a remote location from the processing unit 32.

Figure 3:
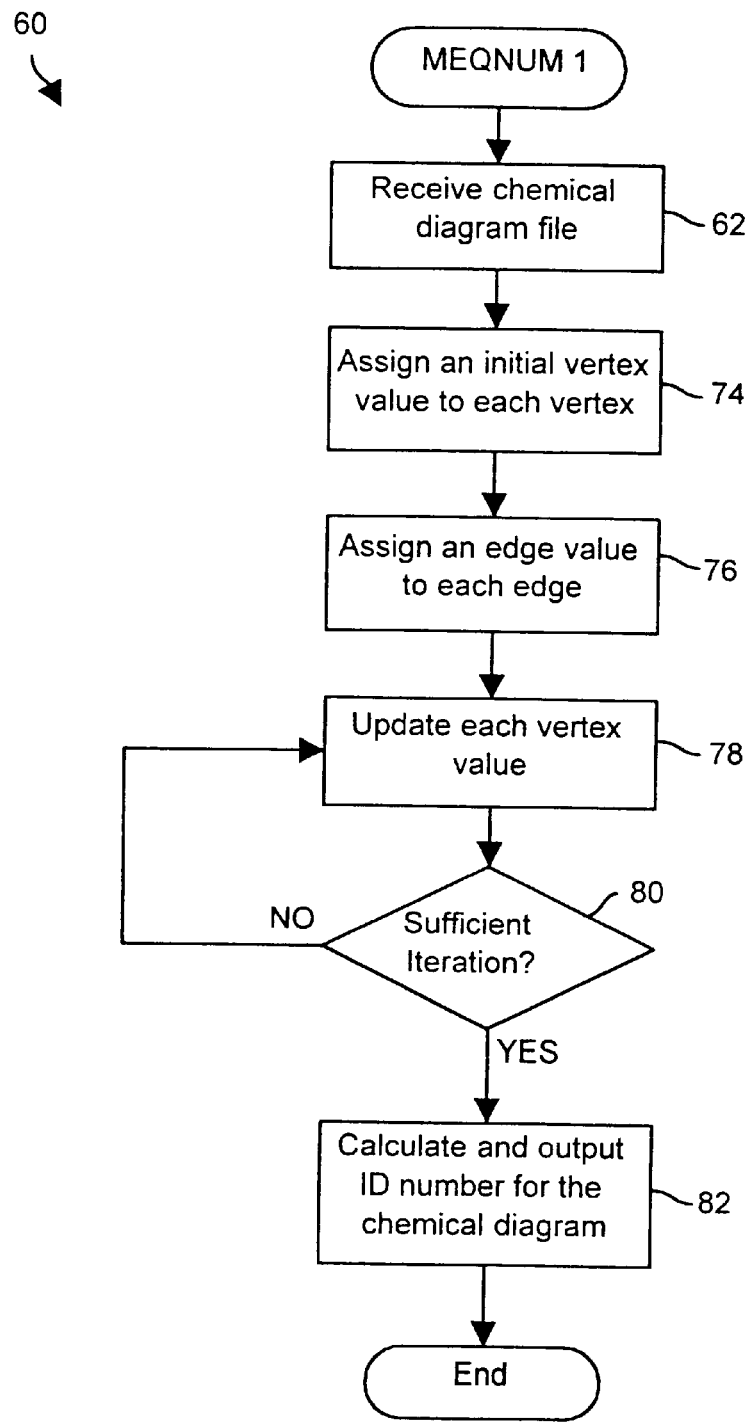
FIG. 3 is a flow diagram illustrating a first molecular equivalence number process that may be used for identifying chemical structures.
Figure 4:
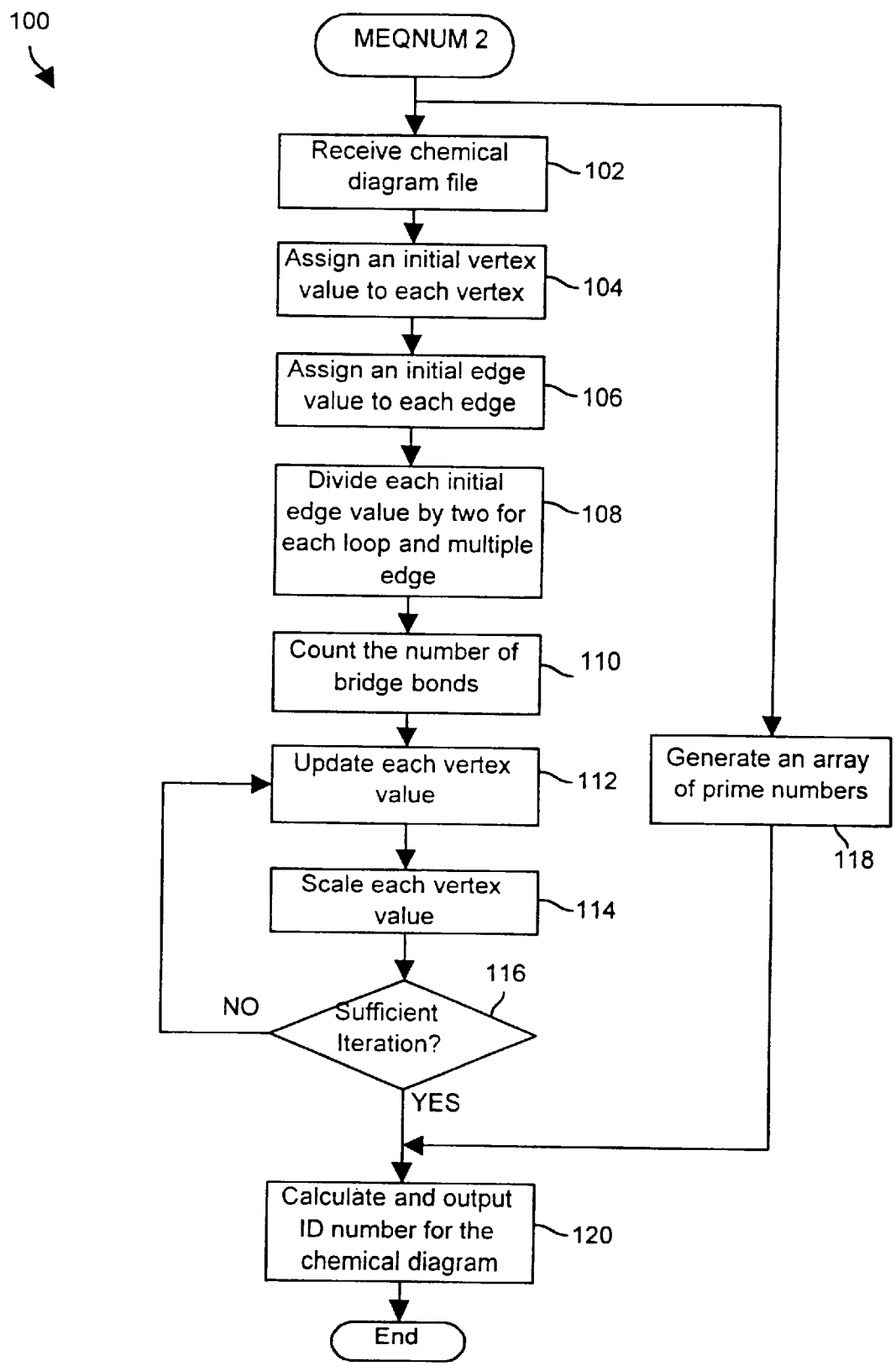
FIG. 4 is a flow diagram illustrating a second molecular equivalence number process that may be used for identifying chemical structures.

As will be appreciated by those having ordinary skill in the art, the memory 40, which may be any computer readable medium, may store instructions in the form of a computer program or computer code. Such instructions are written in such a manner and format so as to be executed by the processor 38. For example, a computer program may be written in various languages such as FORTRAN, Pascal, C or C++ or any other suitable language and compiled to run on the processor 38. FIGS. 3 and 4 are representative of steps or functions of processes or computer programs that may be stored in the memory 40 and executed by the processor 38 to perform the function of naming chemical structures, molecules, pseudographs and the like. As the steps of the processes shown in FIGS. 3 and 4 are described, reference will be made to FIGS. 5–9, wherein the results of the steps are shown with respect to exemplary chemical structures and pseudographs. In particular, the steps shown in FIG. 3 will be explained with respect to FIGS. 5, 6, and 7A–7E (generally, FIG. 7) and the steps shown in FIG. 4 will be explained with respect to FIGS. 5, 6, 8A–8E (generally, FIG. 8) and FIGS. 9A–9H (generally, FIG. 9).

Referring back to FIG. 2, the I/O circuit 42 may be a conventional I/O circuit, such as may be found in any commercially available processing unit 32. The I/O circuit 42 is adapted to transfer information between the video display 34, the input device 36 or any other suitable peripheral and the processor 38. The I/O circuit 42 may be adapted to communicate in a parallel or serial fashion.

Turning now to FIG. 3, a molecular equivalence number 1 (MEQNUM 1) process 60 includes a number of steps, the result of which is a unique number that may be used to identify a chemical structure. At step 62, the process 60 receives a chemical diagram file representative of the chemical structure on which the process 60 is to operate. Generally, such a file may be a text file listing the atoms of the chemical structure, which atoms are bonded together and the types of bonds between atoms. In particular, the file may be an SDfile (structure-data file), the format of which is specified by Molecular Design Limited (MDL), that has been pre-processed to recognize the bond types, side chains, rings and bridges of the chemical structure.

Figure 5:
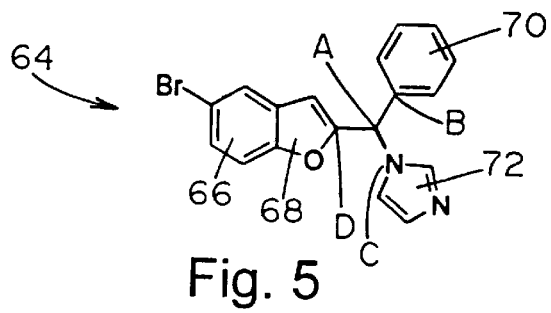
FIG. 5 is an exemplary chemical structure on which the processes of FIGS. 3 and 4 may operate.

The file may represent a chemical structure 64, such as the one shown in FIG. 5. Generally speaking, the chemical structures shown in FIGS. 5–9 do not show hydrogen atoms that may be attached to the various atoms that form the chemical structures shown in these figures. As will be appreciated by those having ordinary skill in the art, the chemical structure 64 of FIG. 5 includes four cyclic rings 66–72 either fused or having bonds therebetween. Two of the cyclic rings 66, 70, are composed purely of carbon atoms (represented by graph vertices having no alphabetical designator). One of the cyclic rings 68 is composed of carbon atoms and a single oxygen atom (represented by the graph vertex having an "O" designation), and one of the cyclic rings 72 is composed of carbon atoms and two nitrogen atoms (represented by the graph vertices having "N" designations). As shown in FIG. 5, four vertices have been labeled with alphabetical designators A–D. These vertices have been labeled with identical designators in FIGS. 6–8 to facilitate reference to these vertices during the description provided below.

Figure 6:
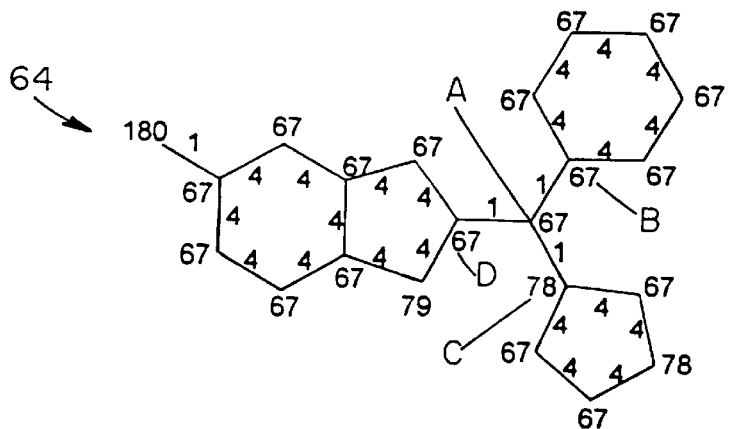
FIG. 6 illustrates the exemplary chemical structure of FIG. 5, on which the vertices and edges have been assigned initial values.

Returning to FIG. 3, after step 62 is complete, step 74 assigns an initial vertex value to each vertex of the chemical structure provided in step 62. The initial vertex values may be assigned in many ways, as long as each atom type represented by a vertex corresponds to a unique value. For example, all carbon atoms may be assigned an initial value of one and all oxygen atoms may be assigned an initial value of two. Alternatively, each vertex may be assigned a value that is the sum of the American Standard Code for Information Interchange (ASCII) characters that make up the symbol name of the atom represented by each vertex. For example, all vertices representing carbon atoms, oxygen atoms, nitrogen atoms and bromine atoms may be assigned values of 67, 79, 78 and 180, respectively. These initial vertex values correspond to the sum of the ASCII characters of each symbol C, O, N and Br, respectively. FIG. 6 shows the chemical structure 64 labeled with the initial vertex values corresponding to the ASCII code of the chemical symbol represented by the vertices. In particular, note that vertices A–D have initial values of 67, 67, 78 and 67, respectively, because vertices A–D represent atoms of carbon, carbon, nitrogen and carbon, respectively. Mathematically, the vertex values may be represented by $v_i$, wherein i is an index that may change values to represent of each vertex. For example, in FIG. 6, $v_A$, $v_B$, $v_C$ and $v_D$ are 67, 67, 78 and 67, respectively. Alternatively, if each vertex is referred to by a sequential number, $v_1, v_2, v_3 \ldots v_n$ may be used to refer to the values of those vertices.

Step 76 assigns an edge value to each edge representing a bond. The edge values depend on the type of chemical bond represented by the edge on the chemical structure 64. For example, edges representing single, double, triple and aromatic bonds may be assigned edge values of 1, 2, 3 and 4, respectively. As shown in FIG. 6, edges AB, AC and AD each represent single bonds and, therefore, are each assigned a value of 1. However, as also shown in FIG. 6, aromatic bonds, which are represented by many edges connecting vertices in the chemical structure 64, are each assigned a value of 4. While single, double, triple and aromatic bonds may be represented by 1, 2, 3 and 4, respectively, any other numerical representation of these bonds is possible as long as each bond type (e.g., single, double, triple or aromatic) is represented by a different number. Mathematically, edge values may be represented by $e_j$, wherein j is a vertex connected to vertex i. For example, if $v_A$ is a vertex under consideration, $e_B$ represents the edge connecting vertex B to vertex A (also referred to herein as edge AB). As shown in FIG. 6, when considering $v_A$, $e_B$, $e_C$ and $e_D$ are all equal to one.

Although FIG. 3 indicates that step 74 occurs before step 76, those having ordinary skill in the art will readily recognize that the ordering of steps 74 and 76 is not critical. For example, step 76 may occur before or at the same time as step 74. Either way, both step 74 and step 76 should be completed before the process 60 reaches step 78.

After each vertex has been assigned an initial vertex value and each edge has been assigned an edge value, step 78 updates each vertex value based on the value of that vertex, on the vertex values of the vertices connected to that vertex and on the edge values of the edges connected to that vertex. A mathematical representation of one possible update procedure is shown in Equation 2 below.

$$v'_i = v_i + \sum_j (v_j + e_j) \qquad \text{Equation 2}$$

Wherein vertex i is the vertex being updated, $v_i'$ is the updated vertex value $v_i$ is the unupdated value of the vertex being updated, j is an index for each vertex connected to vertex i, $v_j$ is the vertex value for vertex j and $e_j$ is the edge connecting each vertex j to vertex i. After the updated vertex value ($v_i'$) is calculated for each vertex, each vertex value is set equal to the updated vertex value according to Equation 3, below.

$$v_i = v_i' \qquad \text{Equation 3}$$

Figure 7A:
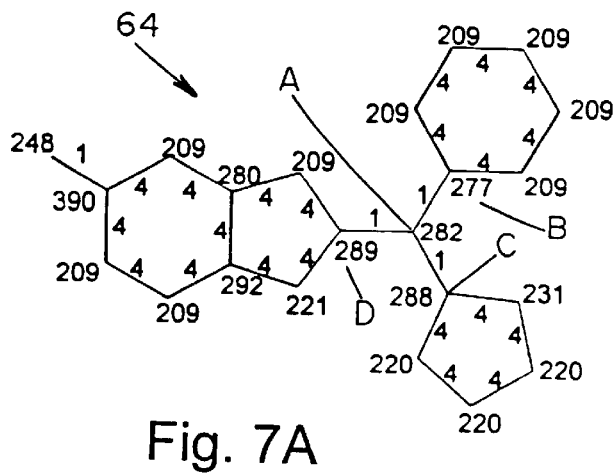
FIGS. 7A–7E illustrate the vertex and edge values of a chemical structure that has been updated various times according to the process of FIG. 3.
Figure 7B:
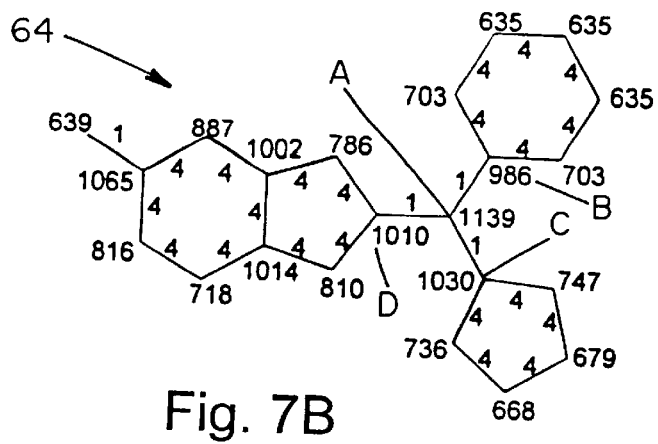
Figure 7C:
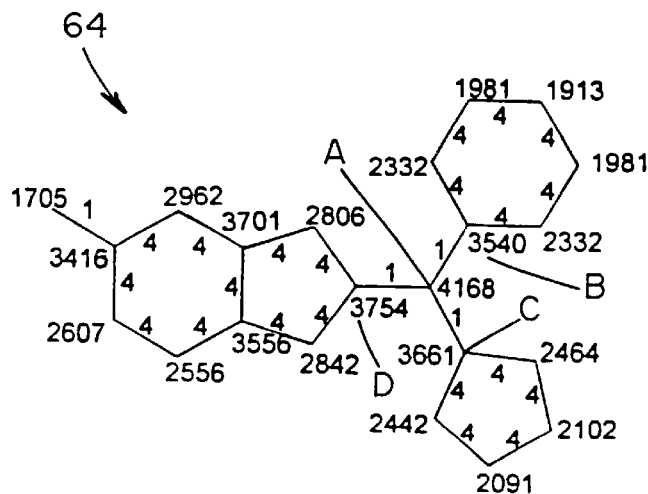
Figure 7D:
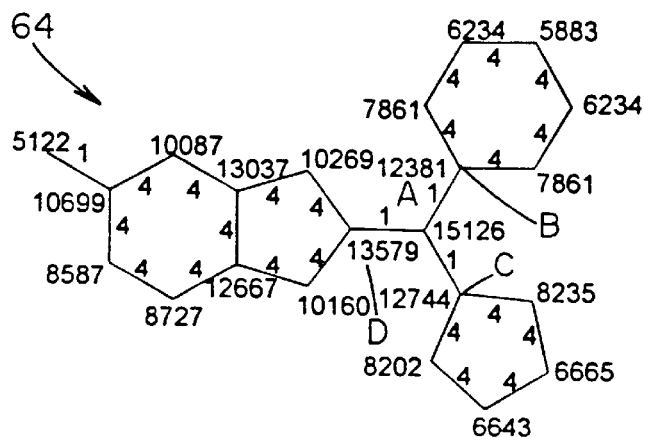
Figure 7E:
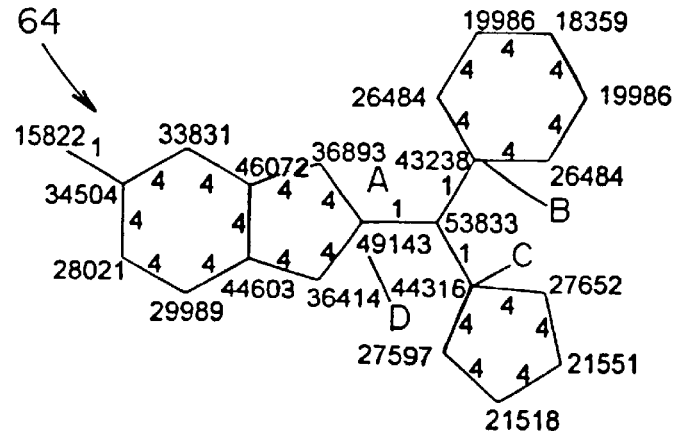

Referring to FIG. 7A, the vertex values of the chemical structure 64 are shown after they have been updated one time. For example, vertex A has a value of 282, which is calculated as follows: 67 (the previous value of vertex A)+[67+1] (the previous value of vertex B and the edge value of the edge connecting vertex B to vertex A)+[78+1] (the previous value of vertex C and the edge value of the edge connecting vertex C to vertex A)+[67+1] (the previous value of vertex D and the edge value of the edge connecting vertex D to vertex A). The other updated values for the other vertices may be calculated in a similar manner. Note, however, that all the values for calculating the updated vertex values shown in FIG. 7A are taken from the vertex values shown in FIG. 6 and are not taken from updated values in FIG. 7A. For example, after vertex A has been updated, vertex B will not be updated using the updated value for vertex A (i.e., the value of vertex A shown in FIG. 7A), but will rather use the unupdated value for vertex A (i.e., the value of vertex A shown in FIG. 6).

After each vertex value has been updated, step 80 of the process 60 determines if sufficient iteration has taken place for the process 60 to converge. The number of iterations may be empirically determined, or a predetermined number of iterations, such as five iterations may be selected. If the number of iterations selected (n) is too small, vertices will lose their uniqueness. However, if the number of iterations selected (n) is too large, the process 60 becomes redundant and computation time increases due to the increased number of iterations. FIGS. 7B, 7C, 7D and 7E show the vertex values of the chemical structure 64 after 2, 3, 4 and 5 executions of step 78, respectively, of the process 60.

The vertex values for FIGS. 7B–7E are calculated using Equations 1 and 2 in a similar manner to the way the vertex values in FIG. 7A are calculated. Each iteration uses only values that were the result of the prior iteration. For example, the vertex values in FIG. 7B were calculated using the vertex values in FIG. 7A, the vertex values in FIG. 7C were calculated using the vertex values in FIG. 7B, and so on.

If step 80 determines that sufficient iteration has not taken place (i.e., the predetermined number of iterations have not been carried out), control passes back to step 80, which updates each vertex value as described above. However, if step 80 determines that sufficient iteration has taken place, control passes to step 82, which outputs an MEQNUM or ID number for the chemical structure provided to the process 60. The MEQNUM may be calculated according to Equation 4, below.

$$m = \prod_i v_i \qquad \text{Equation 4}$$

Wherein m is the ID number for the chemical structure 64 and $v_i$ is the vertex value for vertex i. As shown in Equation 4, the ID number may simply be a product of all of the vertex values shown in FIG. 7E. For example, for the chemical structure 64, after five iterations having the vertex values shown in FIG. 7E, the ID number may be $3.95336 \times 10^{98}$. Repeated execution of the process 60 for different chemical structures will yield a number of identifiers that may be stored in a library in memory (e.g., 40 of FIG. 2). Such libraries may be highly useful in many applications such as drug research or discovery.

As will be appreciated by those having ordinary skill in the art, for large chemical structures having many bonds, high numbers of iterations of the process 60 of FIG. 3 will yield large MEQNUMs. Such large numbers may exceed the ability of the processing unit 32 to store or calculate. The problem of large MEQNUMs is addressed by a process shown in FIG. 4.

Turning now to FIG. 4, a molecular equivalence number 2 (MEQNUM 2) process 100 includes a number of steps, the result of which is a unique number that may be used to identify a chemical structure. Some of the steps shown in FIG. 4 are identical or substantially identical to those shown and described in conjunction with FIG. 3. Where the steps shown in FIG. 4 are similar to the steps described in connection with FIG. 3, reference will be made to a corresponding relevant step shown in FIG. 3. Throughout the description of FIG. 4, reference will be made to FIGS. 5, 6, and 8A–8E.

At step 102, which is analogous to step 62 of FIG. 3, the process 100 receives a chemical diagram file that describes the chemical structure that is to be named or identified by the process 100. For example, the chemical diagram file may describe the chemical structure 64 shown in FIG. 5, which has been previously described.

After the process 100 has received the chemical diagram file, step 104, which is analogous to step 74 of FIG. 3, assigns an initial vertex value to each vertex of the chemical structure 64. A representation of such an assignment may be seen in FIG. 6, which has been previously described. The initial vertex values may be based on the ASCII characters of the chemical symbols of the atoms represented by the vertices of the chemical structure 64. Alternatively, a different numerical assignment may be made to each vertex of the chemical structure 64.

At step 106, the process 100 assigns edge values to the edges of the chemical structure 64. The edges represent bonds between the atoms represented by the vertices. Different types bonds are assigned different values. For example, as described in conjunction with step 76 of FIG. 3, single, double, triple and aromatic bonds may be represented using the numbers 1, 2, 3 and 4, respectively.

At step 108 the edge value for each bond that is a multiple edge or loop is divided by two. While no multiple edges or loops are shown in the chemical structure 64 of FIGS. 5–8, a thorough description of step 108 will be given with respect to FIG. 9, which shows both multiple edges and loops.

A step 110 determines the bridge count for the chemical structure 64. The bridge count of a chemical structure is defined as the count of the number of bridge edges. A bridge edge is an edge that connects two vertices such that when the edge is deleted, two portions of the chemical structure that were previously connected are no longer connected. For example, referring to FIG. 5, if the edge AB were cut, the cyclic ring 70 would become detached from both the cyclic ring 72 and the cyclic ring 68. Therefore, edge AB is a bridge edge. If edge AC were severed, cyclic ring 72 would be detached from both the cyclic ring 70 and the cyclic ring 68. Similarly, if edge AD were severed, the structure having cyclic ring 68 would become detached from both the cyclic ring 70 and the cyclic ring 72. Accordingly edges AB, AC and AD are all bridge edges. Therefore the bridge count for the chemical structure 64 is 3.

Referring back to FIG. 4, step 112 updates each vertex value in a manner analogous to that described in conjunction with step 78, except for the fact that step 112 does not carry out Equation 3, but, rather, carries out only Equation 2. Therefore, the result of step 112 is the vertex value $v_i'$. For example, vertex A would have a $v_i'$ equal to 282. Step 114 scales the vertex value ($v_i'$) according to Equation 5.

$$v_i = (v_i' \bmod \text{maxvtype}) + 1 \qquad \text{Equation 5}$$

In particular, step 114 scales the vertex value $v_i'$ when the vertex value is larger than a variable called maxvtype, while still keeping each vertex value unique. In Equation 5, maxvtype is a variable representing the maximum number of vertex types that the MEQNUM 2 process 100 can accommodate. Commonly, the number of different vertex types is greater than the total number of atoms in the chemical structure. As a worst case, the number of different vertex types is equivalent to the number of atoms in the chemical structure (i.e., each vertex represents a unique atom). Generally, maxvtype may be set to 5000, which would accommodate $4.1 \times 10^{55}$ different vertex value combinations for an average molecule of 20 non-hydrogen atoms.

Figure 8A:
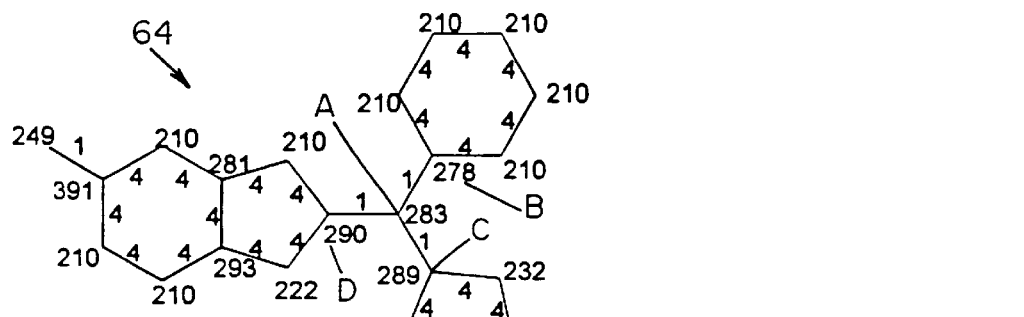
FIGS. 8A–8E illustrate the vertex and edge values of a chemical structure that has been updated various times according to the process of FIG. 4.
Figure 8B:
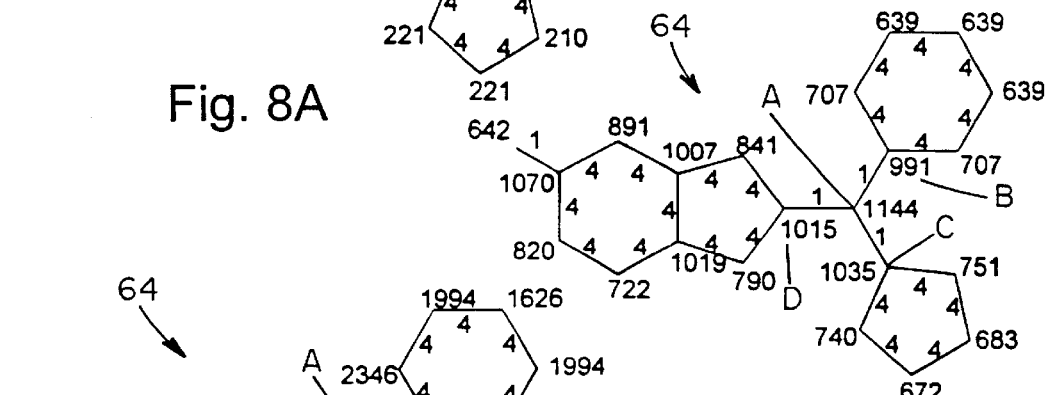
Figure 8C:
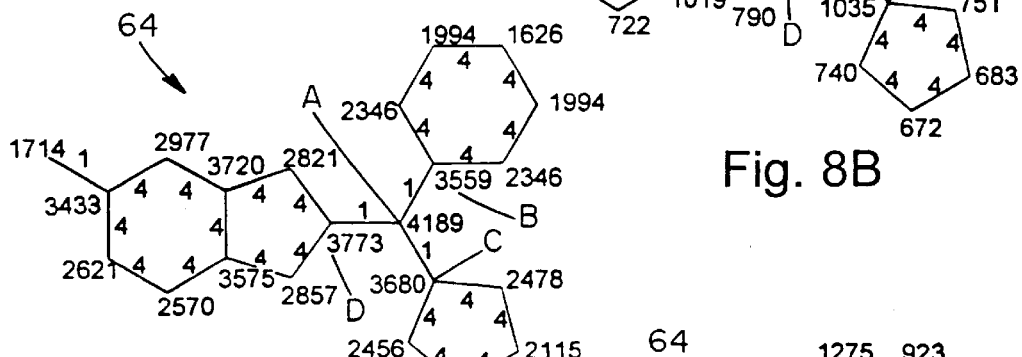

As shown in FIG. 8A, if the maxvtype is 5000, vertex A is equal to 283, which is calculated by step 114 as follows: [282 mod 5000]+1. Obviously, the scaling feature of step 114 will not be realized until $v_i'$ is greater than 5000.

After step 114 is complete, step 116 determines whether sufficient iteration has occurred. This step is analogous to step 80 of FIG. 3, which has been previously described in detail. If the 2 process 100 has not sufficiently iterated, control passes from step 116 back to step 112, which again updates the vertex values according to Equation 2 and passes control to step 114. Step 114 then scales the vertex values calculated by step 112. FIGS. 8B–8E show the results of iterations 2–5 of steps 112 and 114 of the process 100.

Figure 8D:
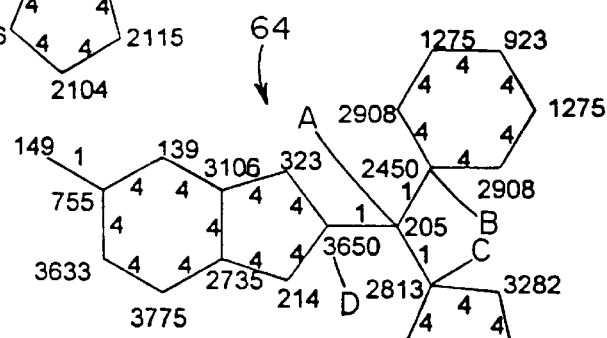

Of particular interest is FIG. 8D, wherein the scaling effects of step 114 may be observed. For example, after the fourth iteration of step 112, vertex A would have had a value of 15,204. However, the scaling performed by step 114 reduced the value of vertex A to 205, which is the result of [15204 mod 5000]+1.

At any time while steps 102–116 are operating, step 118 may generate an array of prime numbers that is equivalent in size to maxvtype. For example, if maxvtype is 5000, step 118 generates an array having the first 5000 prime numbers stored therein.

Figure 8E:
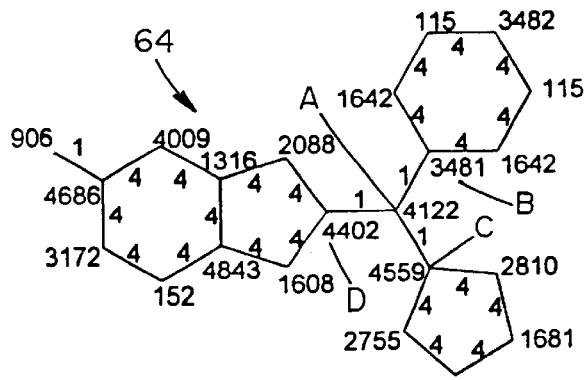

After step 118 generates the array of prime numbers and step 116 determines that the process 100 has sufficiently iterated, the results of which are shown in FIG. 8E, control passes to step 120, which calculates an MEQNUM or ID number for the chemical structure 64 provided in step 102. The ID number may be calculated as shown in Equation 6, below.

$$R = \log(P[(\text{bridge count} \bmod 5000) + 1]) + \sum_i \log(P[v_i]) \qquad \text{Equation 6}$$

Wherein, P[x] is the $x^{th}$ entry in the array of prime numbers generated by step 118, log is the logarithm function and i is an index for vertices. In operation, step 120 sums the logarithms of prime numbers that correspond to the vertex values of each vertex in the chemical structure and adds to that the logarithm of the prime number corresponding to one plus the modulus of the bridge count over 5000. The output of step 120 may be R itself or it may be a desired number of digits of the mantissa of R. The output may use any base numbering scheme, for example, the output may be decimal (base 10) or may be base 35, which yields an alpha-numeric output looking like a license plate number that utilizes numbers 0–9 and letters A–N and P–Z, wherein capital o has been omitted due to possible confusion with the number 0. For example, the result of step 120 may be an R value of 92.158913296087 or the first 6 digits of the mantissa of R (158913). Alternatively, the output of step 120 may be represented by base 35 by removing the decimal point in R to create 92158913296087 and then converting that number to base 35 (15XDLRHAZL). The base 35 MEQNUM from step 120 may then be represented by the last 6 digits of the base 35 version of R (LRHAZL).

Although step 104 is shown in FIG. 4 as occurring before steps 106, 108 and 110, those having ordinary skill in the art will readily recognize that step 104 need not be executed in any particular order with respect to steps 106–110, so long as it occurs before the step 112. Similarly, step 110 does not need to occur in any particular order, so long as step 110 is completed before the execution of step 120.

The operation of the MEQNUM 2 process 100 has been described in conjunction with a chemical structure 364 in FIG. 8. However, the process 100 is also useful in analyzing labeled pseudographs having multiple bonds or loops that, as one having ordinary skill in the art will readily recognize, represent reduced chemical structures. The operation of the process 100 with respect to a pseudograph will be described in conjunction with FIGS. 9A–9H (generally, FIG. 9).

Figure 9A:
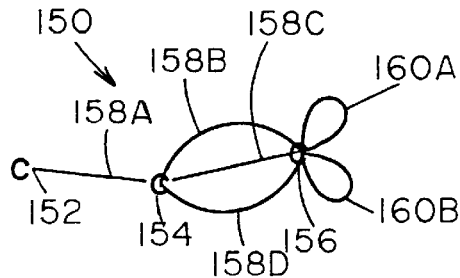
FIGS. 9A–9H illustrate the vertex and edge values of a pseudograph that has been updated various times according to the process of FIG. 4.

FIG. 9A illustrates a chemical pseudograph 150 having three vertices 152, 154 and 156, which represent carbon atoms. The vertices 152–156 are interconnected by a number of bonds that may be represented by edges 158A, 158B, 158C, 158D and loops 160A, 160B. Step 102 of FIG. 4 receives a file representing the pseudograph 150 and step 104 assigns initial vertex values to the vertices of the pseudograph 150 based on the atoms represented by the vertices of the pseudograph. These vertex values are shown in FIG. 9B.

Figure 9B:
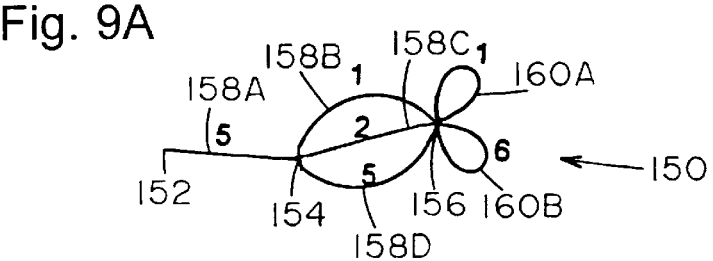

As shown in FIG. 9B, the carbon atoms are represented by 67, which is the ASCII code for the chemical symbol for carbon (C). Step 106 assigns an initial edge value to each edge and loop based on the bonds that the edges and loops represent. Initial edge values depend on the types of bonds that the edges represent. For example, single, double, triple and aromatic bond types may have initial edge values equal to 1, 2, 3 and 4, respectively. Because an edge 158 or a loop 160 on a pseudograph may represent a number of bonds, the initial edge values shown in FIG. 9B may be values that are combinations of 1, 2, 3 and 4. For example, as shown in FIG.

9B, edges 158A, 158B, 158C and 158D may have initial values of 5, 1, 2 and 5, respectively. Further, loops 160A and 160B may have initial values of 1 and 6, respectively.

Figure 9C:
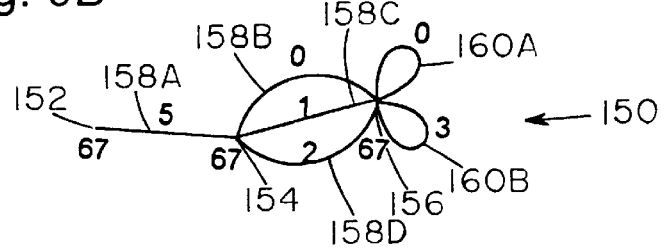

Step 108 uses integer division to divide the initial edge values by a factor of two. For example, as shown in FIG. 9C, edges 158A, 158B, 158C and 158D may have values of 5, 0, 1 and 2, respectively, and loops 160A and 160B may have values of 0 and 3, respectively. As will be appreciated by those having ordinary skill in the art, integer division of 1 divided by 2 is equal to 0 and integer division of 5 divided by 2 is equal to 2.

Step 110 counts the number of bridge bonds of the pseudograph 150, which has no bridge bonds. Step 112 updates the value of each vertex. An updated vertex value may be calculated according to Equation 2. For example, updated vertex value of vertex 156 may be 408, which is calculated as follows: 67 (the previous value of vertex 156)+[67+0] (the previous value of vertex 156 and the edge value of the loop 160A connecting vertex 156 to itself)+ [67+3] (the previous value of vertex 156 and the edge value of the loop 160B connecting vertex 156 to itself)+[67+0] (the previous value of vertex 154 and the edge value of the edge 158B connecting vertex 154 to vertex 156)+[67+1] (the previous value of vertex 154 and the edge value of the edge 158C connecting vertex 154 to vertex 156)+[67+2] (the previous value of vertex 154 and the edge value of the edge 158D connecting vertex 154 to vertex 156).

Figure 9D:
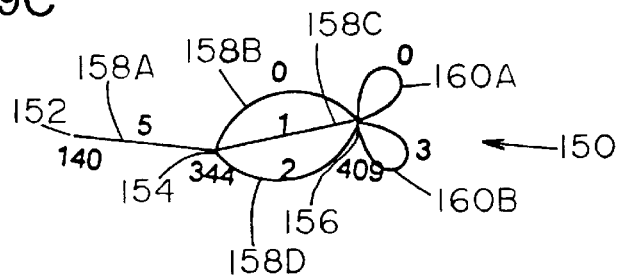
Figure 9E:
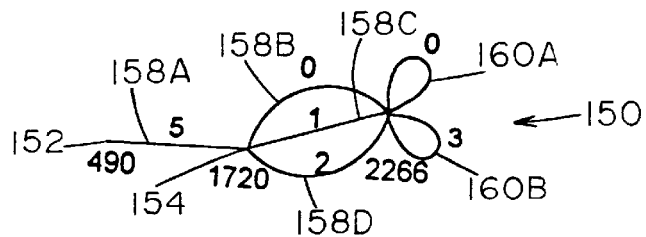
Figure 9F:
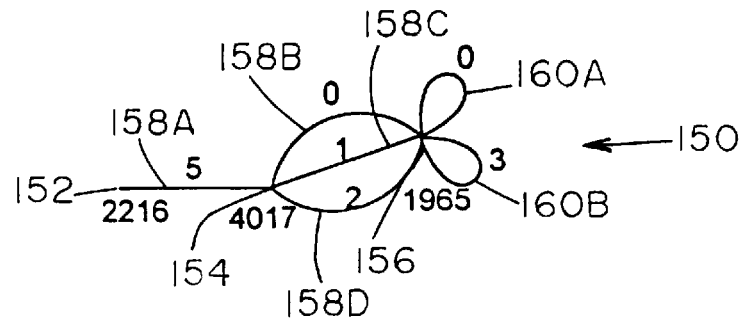
Figure 9G:
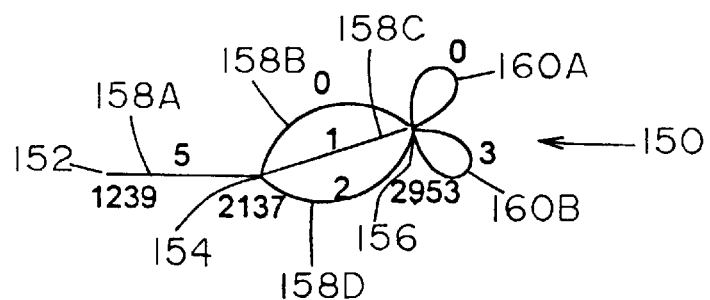
Figure 9H:
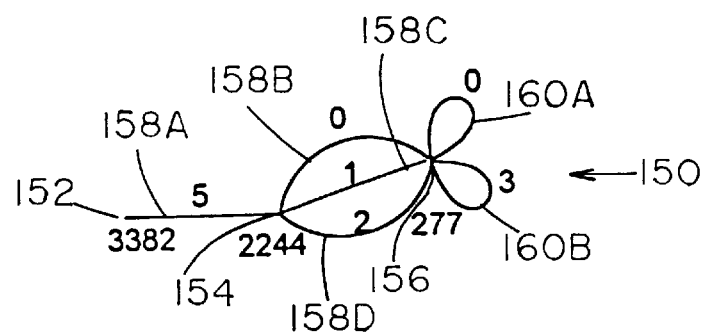

After step 112 has updated each vertex value, step 114 scales each vertex value using Equation 5. For example, if the updated vertex value for vertex 156 is 408 and the maxvtype is 5000, the scaled vertex value for vertex 156 is [408 mod 5000]+1, or 409, as shown in FIG. 9D. The other vertices are similarly treated. After step 112 operates, step 116 determines whether the process 100 has sufficiently iterated. If the process 100 has not sufficiently iterated, control passes back to step 112. FIGS. 9D–9H show the various values of the pseudograph vertices 152–156 after one to five executions of steps 112 and 114, respectively.

After step 116 determines that the process 100 has iterated sufficiently, step 120 calculates the MEQNUM for the pseudograph 150. This is carried out as described above in connection with step 120. The result of step 120 for the pseudograph 150 after the fifth iteration is 12.046437917010, which may be represented by 46437. Alternatively, when expressed in base 35 the MEQNUM may be 5DS10Z. Repeated execution of the process 120 for different chemical structures will yield a number of identifiers that may be stored in a library in memory (e.g., 40 of FIG. 2). Such libraries may be highly useful in many applications such as drug research or discovery.

As will be appreciated by those having ordinary skill in the art, the foregoing described processes are useful for assigning accurate and unique numeric or alpha-numeric identifiers to chemical structures or pseudographs. The identifiers, in and of themselves, have no particular significance other than representing a unique way of identifying a number of attributes and/or atomic connectivity patterns for a given chemical molecule. More specifically, the identifier may act as a fingerprint of a labeled pseudograph derived from the molecule that embodies the attributes and/or atomic connectivity patterns such as the number and type of atoms, bonds, ring structures, et cetera.

The invention may be used for technical searching of libraries of compounds and analyzing relationships amongst libraries. Such uses may be related to various physiochemical and pharmacological properties associated with the constituent compounds. Such use may involve traditional database searching engines and retrieval programs capable of sorting data fields by "rows" and "columns" that can be accessed by statistical and visual analysis software. Examples of such software include Excel, Jump, SAS, Splus, Spotfire and the like. Recognizing which software packages have these capabilities is considered to be well within the skill of one having ordinary skill in the art. If, for example, a researcher wanted to identify all molecules in a given library having certain specific identifying criteria or attributes, the researcher simply would search by such relevant criteria and the software would indicate the compounds satisfying the search criteria. The researcher could then use the results of the search to analyze similarities and differences between given compounds.

The invention may be particularly useful in the field of drug development and discovery. If key attributes of a molecule are known to be desirable, if not critical for success of the molecule as a potential drug candidate, conducting the attribute searches as discussed above provides a very fast and reliable way for the researcher to identify compounds for testing and initial selection of lead candidates. In addition to this use, the separate identification for each separate molecule can be used to determine whether compound collections under evaluation are of interest, and in comparing different compound collections. In addition to the above, it is expected that other uses would readily be envisioned where it is desirable to have molecules identified by their specific identifying criteria.

Numerous modifications and alternative embodiments of the invention will be apparent to those having ordinary skill in the art in view of the foregoing description. Accordingly, this description is to be construed as illustrative only and not as limiting to the scope of the invention. The details of the structure may be varied substantially without departing from the spirit of the invention, and the exclusive use of all modifications, which are within the scope of the appended claims, is reserved.

What is claimed is:

1. A method of generating an identifier representative of a chemical structure having a first atom, a second atom and a bond connecting the first atom and the second atom, the method comprising the steps of:

representing the first atom with a first numerical value;

representing the second atom with a second numerical value;

representing the bond with a numerical bond value;

calculating an updated first numerical value based on the first numerical value, the second numerical value and the numerical bond value;

calculating an updated second numerical value based on the second numerical value, the first numerical value and the numerical bond value;

calculating the identifier based on the updated first numerical value and the updated second numerical value; and determining a number of bridge bonds that are found in the chemical structure.

2. The method of claim 1, wherein the step of calculating the identifier is based on the number of bridge bonds.

3. A method of generating an identifier representative of a chemical structure having a first atom, a second atom and a bond connecting the first atom and the second atom, the method comprising the steps of:

representing the first atom with a first numerical value;

representing the second atom with a second numerical value;

representing the bond with a numerical bond value;

calculating an updated first numerical value based on the first numerical value, the second numerical value and the numerical bond value;

calculating an updated second numerical value based on the second numerical value, the first numerical value and the numerical bond value; and calculating the identifier based on the updated first numerical value and the updated second numerical value, the first and second atoms represented by first and second chemical symbols having first and second sets of characters and the steps of representing the first and second atoms with first and second numerical values comprise the steps of setting the first numerical value equivalent to an ASCII code sum of the first set of characters and setting the second numerical value equivalent to an ASCII code sum of the second set of characters.

4. For operation on a processor, a system for generating an identifier representative of a chemical structure having a first atom, a second atom and a bond connecting the first atom and the second atom, the system comprising:

a computer readable medium;

a first portion of software stored on the computer readable medium and adapted to be executed on the processor to represent the first atom with a first numerical value and to represent the second atom with a second numerical value;

a second portion of software stored on the computer readable medium and adapted to be executed on the processor to represent the bond with a numerical bond value;

a third portion of software stored on the computer readable medium and adapted to be executed on the processor to calculate an updated first numerical value based on the first numerical value, the second numerical value and the numerical bond value;

a fourth portion of software stored on the computer readable medium and adapted to be executed on the processor to calculate an updated second numerical value based on the second numerical value, the first numerical value and the numerical bond value;

a fifth portion of software stored on the computer readable medium and adapted to be executed on the processor to calculate the identifier based on the updated first numerical value and the updated second numerical value; and a sixth portion of software stored on the computer readable medium and adapted to be executed on the processor to determine a number of bridge bonds found in the chemical structure.

5. The system of claim 4, wherein the fifth portion of software is adapted to be executed on the processor to calculate the identifier based on the number of bridge bonds found in the chemical structure.

6. For operation on a processor, a system for generating an identifier representative of a chemical structure having a first atom, a second atom and a bond connecting the first atom and the second atom, the system comprising:

a computer readable medium;

a first portion of software stored on the computer readable medium and adapted to be executed on the processor to represent the first atom with a first numerical value and to represent the second atom with a second numerical value;

a second portion of software stored on the computer readable medium and adapted to be executed on the processor to represent the bond with a numerical bond value;

a third portion of software stored on the computer readable medium and adapted to be executed on the processor to calculate an updated first numerical value based on the first numerical value, the second numerical value and the numerical bond value;

a fourth portion of software stored on the computer readable medium and adapted to be executed on the processor to calculate an updated second numerical value based on the second numerical value, the first numerical value and the numerical bond value; and a fifth portion of software stored on the computer readable medium and adapted to be executed on the processor to calculate the identifier based on the updated first numerical value and the updated second numerical value, the first and second atoms represented by first and second chemical symbols having first and second sets of characters and the first portion of software, when executed on the processor, causes the processor to set the first numerical value equivalent to an ASCII code sum of the first set of characters and to set the second numerical value equivalent to an ASCII code sum of the second set of characters.

7. A method of generating an identifier representative of a chemical structure having a first atom, a second atom and a bond connecting the first atom and the second atom, the method comprising the steps of:

representing the first atom with a first numerical value;

representing the second atom with a second numerical value;

representing the bond with a numerical bond value;

determining a number of bridge bonds that are found in the chemical structure;

calculating an updated first numerical value based on the first numerical value, the second numerical value and the numerical bond value;

calculating an updated second numerical value based on the second numerical value, the first numerical value and the numerical bond value; and calculating the identifier based on the updated first numerical value, the updated second numerical value and the number of bridge bonds.

8. The method of claim 7, further comprising the step of repeating the steps of calculating the updated first and second numerical values.

9. The method of claim 7, wherein the first and second atoms may be represented by first and second chemical symbols having first and second sets of characters and wherein the steps of representing the first and second atoms with first and second numerical values comprise the steps of setting the first numerical value equivalent to an ASCII code sum of the first set of characters and setting the second numerical value equivalent to an ASCII code sum of the second set of characters.

10. The method claim 7, wherein the bond connecting the first atom and the second atom has a bond type and wherein the step of representing the bond with a numerical bond value comprises representing the bond with a numerical bond value that is related to the bond type.

11. The method of claim 10, further comprising the step of dividing the numerical bond identifier by a factor of two if more than one bond connects the first atom and the second atom.

12. The method claim 7, further comprising the step of generating an array of prime numbers, the array having a size at least as large as the updated first numerical value and the updated second numerical value, wherein the step of calculating the identifier is based on the array of prime numbers.

13. For operation on a processor, a system for generating an identifier representative of a chemical structure having a first atom, a second atom and a bond connecting the first atom and the second atom, the system comprising:
  a computer readable medium;
  a first portion of software stored on the computer readable medium and adapted to be executed on the processor to represent the first atom with a first numerical value and to represent the second atom with a second numerical value;
  a second portion of software stored on the computer readable medium and adapted to be executed on the processor to represent the bond with a numerical bond value;
  a third portion of software stored on the computer readable medium and adapted to be executed on the processor to determine a number of bridge bonds found in the chemical structure;
  a fourth portion of software stored on the computer readable medium and adapted to be executed on the processor to calculate an updated first numerical value based on the first numerical value, the second numerical value and the numerical bond value;
  a fifth portion of software stored on the computer readable medium and adapted to be executed on the processor to calculate an updated second numerical value based on the second numerical value, the first numerical value and the numerical bond value; and
  a sixth portion of software stored on the computer readable medium and adapted to be executed on the processor to calculate the identifier based on the updated first numerical value, the updated second numerical value and the number of bridge bonds.

14. The system of claim 13, wherein the first and second atoms may be represented by first and second chemical symbols having first and second sets of characters and wherein the first portion of software, when executed on the processor, causes the processor to set the first numerical value equivalent to an ASCII code sum of the first set of characters and to set the second numerical value equivalent to an ASCII code sum of the second set of characters.

15. The system of claim 14, further a comprising a seventh portion of software stored on the computer readable medium and adapted to be executed on the processor to divide the numerical bond identifier by a factor of two if more than one bond connects the first atom and the second atom.

16. The system of claim 13, wherein the bond connecting the first atom and the second atom has a bond type and wherein the second portion of software, when executed on the processor, causes the processor to represent the bond with a numerical bond value that is related to the bond type.

17. The system of claim 13, further comprising an eighth portion of software stored on the computer readable medium and adapted to be executed on the processor to generate an array of prime numbers, the array having a size at least as large as the updated first numerical value and the updated second numerical value, wherein the sixth portion of software, when executed on the processor, causes the processor to calculate the identifier based on the array of prime numbers.

18. A method of compiling a library for drug research, the library including a plurality of identifiers representative of a plurality of chemical structures, the method comprising the steps of:
  selecting a chemical structure from the plurality of chemical structures, the selected chemical structure having a first atom, a second atom and a bond connecting the first atom and the second atom;
  representing the first atom with a first numerical value;
  representing the second atom with a second numerical value;
  representing the bond with a numerical bond value;
  determining a number of bridge bonds that are found in the chemical structure;
  calculating an updated first numerical value based on the first numerical value, the second numerical value and the numerical bond value;
  calculating an updated second numerical value based on the second numerical value, the first numerical value and the numerical bond value;
  calculating the identifier based on the updated first numerical value, the updated second numerical value and the number of bridge bonds; and
  storing the identifier in a memory.

19. The method of claim 18, wherein the method is repeated for each chemical structure in the plurality of chemical structures, thereby storing the plurality of identifiers in the memory.

20. The method of claim 19, further comprising the steps of searching the memory for chemical structures having a desired attribute and outputting a list of chemical structures having the desired attribute.

21. The method of claim 20, further comprising the step of using the list of chemical structures having the desired attribute to select a compound for medical treatment.

22. The method of claim 19, further comprising the steps of sorting the plurality of identifiers in the memory according to a desired attribute and outputting a sorted list of chemical structures sorted according to the desired attribute.

23. The method of claim 22, further comprising the step of using the sorted list of chemical structures to select a compound for medical treatment.

24. The method of claim 19, wherein the library is a first library, the plurality of identifiers is a first plurality of identifiers and the plurality of chemical structures is a first plurality of chemical structures, the method further comprising the step of compiling a second library including a second plurality of identifiers representative of a second plurality of chemical structures.

25. The method of claim 24, further comprising the step of comparing the first plurality of identifiers with the second plurality of identifiers.

* * * * *

UNITED STATES PATENT AND TRADEMARK OFFICE
CERTIFICATE OF CORRECTION

PATENT NO. : 6,757,618 B2
DATED : June 29, 2004
INVENTOR(S) : Mark A. Johnson et al.

It is certified that error appears in the above-identified patent and that said Letters Patent is hereby corrected as shown below:

Column 16,
Line 59, cancel "method claim" and insert -- method of claim --.

Column 17,
Line 1, cancel "method claim" and insert -- method of claim --.

Signed and Sealed this

Twelfth Day of October, 2004

JON W. DUDAS
*Director of the United States Patent and Trademark Office*